United States Patent
Guyon et al.

(10) Patent No.: US 8,357,915 B2
(45) Date of Patent: Jan. 22, 2013

(54) METHOD AND DEVICE FOR MEASURING OPTICAL CHARACTERISTICS OF AN OBJECT

(75) Inventors: Laurent Guyon, Grenoble (FR); Lionel Herve, Villeurbanne (FR)

(73) Assignee: Commissariat a l'Energie Atomique Et Aux Energies Alternatives (FR)

( * ) Notice: Subject to any disclaimer, the term of this patent is extended or adjusted under 35 U.S.C. 154(b) by 745 days.

(21) Appl. No.: 12/606,437

(22) Filed: Oct. 27, 2009

(65) Prior Publication Data

US 2010/0102210 A1    Apr. 29, 2010

(30) Foreign Application Priority Data

Oct. 28, 2008 (FR) ..................... 08 57331

(51) Int. Cl.
*G01J 1/58* (2006.01)
*G01J 1/08* (2006.01)
(52) U.S. Cl. .................................. 250/458.1
(58) Field of Classification Search ........... 250/458.1, 250/459.1, 461.2; 600/476; 382/128, 131, 382/133
See application file for complete search history.

(56) References Cited

U.S. PATENT DOCUMENTS 5,485,530 A * 1/1996 Lakowicz et al. ............ 382/191
2007/0195298 A1  8/2007 Hares et al.

FOREIGN PATENT DOCUMENTS

GB    2 416 945 A    2/2006

OTHER PUBLICATIONS

Soloviev et al., "Fluorescence lifetime imaging by using time-gated data acquisition", Applied Optics, Oct. 20, 2007, pp. 7384-7391, vol. 46, No. 30, Optical Society of America US.
Laidevant et al., "Time-Resolved Imaging of a Fluorescent Inclusion in a Turbid Medium Using a Gated CCD Camera", OSA/BOSD, AOIMP, TLA, 2006, p. SH52, Optical Society of Ameri.
D'Andrea et al., "Time-resolved optical imaging through turbid media using a fast data acquisition system based . . . ", J. Phys. D: Appl. Phys., Jul. 1, 2003, pp. 1675-1681, 36 UK.
Schweiger et al., "Direct calculation with a finite-element method of the Laplace transform . . . ", Applied Optics, Dec. 1, 1997, p. 9042-9049, vol. 36, No. 34, Opt. Soc. of Am US.
Gributs et al., "Optical property determination of turbid media by Time-Resolved Transmittan . . . ", Canadian J. of Analyt. Scien. and Spec., 2004, p. 193-201, vol. 49, No. 3, CA.
Mizeret et al., "Instrumentation for real-time fluorescence lifetime imaging in endoscopy", Review of Scientific Instruments, Dec. 1, 1999, p. 4689-4701, vol. 70, No. 12, US.
Rapport De Recherche Preliminaire, Jun. 12, 2009, Institut National de la Propriete Industrielle for French Patent Application No. 0857331, 4 pages.

* cited by examiner

*Primary Examiner* — David Porta
*Assistant Examiner* — Yara Green
(74) *Attorney, Agent, or Firm* — Cantor Colburn LLP

(57) ABSTRACT

Method and device for measuring the multi-dimensional distribution of optical characteristics of an object, by carrying out the following operations:
  illumination of the object by means of a pulsed light source; and
  acquisition of an image by modulated detection of light rays coming from the object consecutively to the illumination, the detection being modulated according to an acquisition modulation function G(t) which is continuous, non-sinusoidal and temporal, the acquisition taking place outside the phase of illumination by the light source.

17 Claims, 3 Drawing Sheets

*4a*

*4b*

*4c*

METHOD AND DEVICE FOR MEASURING OPTICAL CHARACTERISTICS OF AN OBJECT

This application is a U.S. national phase application filed pursuant to 35 U.S.C. 119 and claims priority to and benefit of French Patent Application No. 08 57331, filed Oct. 28, 2008.

TECHNICAL FIELD

The present invention relates to the technical field of diffuse optical imaging and to its application to diffuse optical fluorescence imaging and to the determination of optical properties of scattering media. The invention may in particular be applied to biological tissue specimens or to animal or human body parts, the dimensions of which are compatible with the penetration depth of the optical radiation used.

PRIOR ART

Diffuse optical imaging generally consists in determining the distribution of optical properties of a living or non-living biological object in order to deduce therefrom the existence or absence of a pathology. It may also consist in determining the average optical properties of a medium. This technique may be employed directly on the biological object without altering its chemical or physical composition, or after injecting fluorescent labels that will be localized.

In the field of localizing tumours, for example, the first technique consists in exploiting the fact that tumours are highly vascularized with an anarchic blood network. This strong vascularization locally modifies the optical absorption properties due to the modification in concentration of chromophores, such as haemoglobin, or the scattering properties due more to the modification in local structure of the scattering structures. This therefore requires the use of a wavelength range of non-ionizing radiation, such as light radiation, in the red or near infrared, where biological tissues have a minimum absorption so as to detect the presence of an abnormally absorbent and/or scattering area.

The second technique, called fluorescence imaging, employs specific fluorescent labels that are preferentially fixed onto target cells of interest, for example cancerous tumours. Fluorescent labels then offer a better detection contrast than that for example offered by the highly vascularized areas used in the first technique. Optical fluorescence imaging is therefore aimed at spatially localizing the fluorescent labels, while determining the concentration thereof. This allows indirect localizing of the tumour and provides information about its shape and its biological activity.

Diffuse optical imaging may be used by illuminating a medium, such as a biological tissue, with a light source and by detecting the light scattered by the medium. Depending on the relative positioning of the source and the detector with respect to the medium, the imaging is either carried out in reflection mode or in transmission mode.

There are three diffuse optical imaging methods that may be distinguished according to whether the light source used is continuous, frequential (i.e. the intensity of the light is modulated by a sinusoidal time function) or pulsed.

Instruments employing a continuous light source were the first to be used, the light source being a filtered white source or a monochromatic source such as a laser. Light detectors or two-dimensional detectors are then used for measuring the intensity of the light reflected or transmitted by a tissue illuminated by the light source.

The second category of diffuse optical imaging, called frequential imaging, uses a light source intensity-modulated at a given frequency. The light source is usually a laser source intensity-modulated at frequencies f generally ranging between a few tens of kHz to a few hundred MHz. The detector used, which too is intensity-modulated at the same frequency f as the excitation or at a harmonic frequency, measures both the amplitude of the light signal reflected or transmitted by the tissue and the phase of this light signal with respect to that of the light source. U.S. Pat. No. 5,485,530 describes a device and a method for fluorescence imaging that may be put into this category. The above application describes a sinusoidal modulation of the amplitude of the excitation light and of the detector, the modulation of the source and the modulation of the detector being carried out at the same frequency or at harmonic frequencies. This technique therefore amounts to synchronously detecting the fluorescence signal, a technique well known to those skilled in the art.

Finally, the third diffuse optical imaging category is pulsed diffuse optical imaging or temporal diffuse optical imaging or time-resolved diffuse optical imaging. The source used produces light pulses of short duration, with a given pulse repetition frequency. The sources used may be picosecond pulsed laser diodes, or femtosecond lasers. Since the pulse duration is generally less than 1 ns, the light sources are then referred to as subnanosecond pulsed light sources. The pulse repetition rate is usually between a few hundred kHz and few hundred MHz.

The invention relates to this third fluorescence imaging category, since the inventors considered that the temporal data is the data containing the most information about the tissue or object scanned. The aim of this approach is to record at each acquisition point the photon time-of-flight histogram, also called the TPSF (temporal point spread function). The aim of the methodology employed is then to extract simple parameters from the TPSF, the theoretical expression of which is known, in order thereafter to solve what is called an inverse problem so as to recover the distribution of the absorption, scattering or fluorescence areas.

In the context for example of time-resolved fluorescence imaging, the light therefore penetrates into the scattering object scanned by a first face, while a photon sensor is located facing a second face of the object in order to detect the photons emitted by this second face as a result of the excitation or the light pulse emitted by the source. The second face may be the same as the first face, which corresponds to a reflection mode of operation. The purpose of the measurements is therefore to detect the temporal distribution of the light emitted by the second face of the object and more particularly the number of photons emitted as a function of time over a time range between a time $T_0$ corresponding to the excitation and a time $T_0+D$, where D may for example be between 1 and 20 ns and usually between 5 and 10 ns. Since the duration of the excitation is less than 1 ns, and possibly of the order of a picosecond or a femtosecond, it will therefore be understood that the acquisition of the emitted photons is to a large part, or even completely, carried out when the excitation source is off, i.e. between two successive pulses of this source. It may also be envisaged to start the measurements with a slight delay $\epsilon$, of the order of the duration of the light pulse, and therefore to start measuring at a time $T_0+\epsilon$, this delay making it possible for example to prevent the photodetector from being dazzled by the source. Several techniques may then be envisaged for determining this temporal distribution. A first technique consists in detecting the time of flight of a first photon starting from the pulse emission time using a method called TCSPC (time-correlated single-photon counting) as described for example in patent application FR 2 204 691 [1]. According to this method, a large number of measurements are taken, each consisting in establishing the time of flight of a photon on a detector relative to the exciting pulse. After a large number of measurements, through a statistical effect, a histogram H(t) may be generated that represents the number of photons detected as a function of time elapsed since the excitation. Owing to the fact that the measurement is a point measurement, it is necessary, in order to obtain this histogram at several points on the observed object, to perform a spatial scan. This results in a particularly long acquisition time, depending on both the number of acquisitions necessary at each point and on the desired spatial resolution. To remedy the drawback associated with the spatial resolution of the measurements, it has been proposed to employ a two-dimensional sensor which simultaneously performs TCSPC measurements at several points in space, as described in the U.S. Pat. No. 5,485,530 [2]. The sensor employed may for example be an intensified high-speed camera used so as to obtain a histogram of the number of photons detected as a function of the time elapsed since the excitation, for each pixel. As described in the publication "Fluorescence lifetime imaging by using time-gated data acquisition", Applied Optics 2007, vol. 46, n° 30, pp 7384-7391 by Soloviev et Al, a predefined time-gate of temporal width σ, the opening of which is successively delayed, relative to the excitation, by a given delay step P, is then employed on this camera. The first measurements are carried out between $T_0$ and $T_0+\sigma$, the second measurements between $T_0+P$ and $T_0+P+\sigma$ and the $n^{th}$ measurements between $T_0+nP$ and $T_0+nP+\sigma$. For statistical reasons, several measurements may be carried out for the same time-gate. It therefore appears necessary to also carry out a large number of measurements in order to obtain a histogram representing the temporal distribution of the photons detected for each pixel of an image corresponding to part of the surface of the object located facing the sensor. After these acquisitions, a histogram matrix is obtained from which it is possible to determine quantities of interest relating to the scattering object examined. These quantities may for example correspond to the spatial distribution, such as the absorption coefficient $\mu_a$ or the reduced scattering coefficient $\mu'_s$ or the spatial distribution of the fluorophores in the object observed.

These quantities of interest are determined using signal processing techniques known to those skilled in the art and especially the techniques described in [1] or [2], or else in "Méthode optique résolue en temps pour la tomographie de fluorescence dans les milieux diffusants [Time-resolved optical method for fluorescence tomography in scattering media]", the university doctoral thesis of Aurélie Laidevant, available on tel.archives-ouverte.fr under the reference tel-00122185 [3] and in the bibliography of this thesis. The signal processing employed is aimed for example, but not exclusively, at the determination of Mellin transforms, also called moments, or to the determination of Laplace transforms from recorded distributions. Thus, each histogram corresponding to a pixel of the recorded image requires particularly resource-consuming calculations so as to obtain intermediate data as described above—moments and Laplace transform—in order to recover the quantities of interest, namely, for example, the absorption coefficients, the reduced scattering coefficients or the concentration of fluorophores.

There therefore appears to be a need for a method and a device which make it possible, on the one hand, to reduce the number of acquisitions needed to produce useful measurements for determining the quantities of interest and, on the other hand, to reduce the number of recorded files and therefore their processing time, mainly resulting from their read time, in order to obtain said quantities of interest.

SUMMARY OF THE INVENTION

To achieve this objective, the invention relates to a method of measuring optical characteristics of an object. This measurement method comprises the following operations:
  illumination of the object by means of a light beam using a pulsed light source; and
  acquisition of an image by modulated detection of light rays coming from the object consecutively to the illumination, the detection being modulated according to an acquisition modulation function G(t) which is continuous, non-sinusoidal and temporal, the acquisition taking place outside the phase of light beam emission by the light source.

It should be understood that the modulation of the acquisition also takes place outside the phases of light emission by the light source. The expression "outside" means that the most significant part of the step under consideration, acquisition or modulation, is carried out consecutively to the emission of a light pulse and before the emission of the following light pulse.

The expression "continuous function" describes a function such that f(x) approaches $f(x_0)$ when x approaches $x_0$.

According to one feature of the invention, the light source is a subnanosecond pulsed source and the acquisition is carried out between two light pulses.

According to another feature of the invention, the detection is modulated according to an acquisition modulation function designed so that the result of the modulated acquisition is directly an optical characteristic of the object at each point or pixel of the image or an intermediate quantity enabling this feature to be calculated more rapidly than with the prior techniques.

Thus the modulation of the acquisition carried out upon each illumination makes it possible to obtain, for each pixel, a quantity which is a function of an optical characteristic of interest of the illuminated object without it being necessary to take mathematical processing of the acquisitions so that, with a single acquisition, it is possible to directly obtain a quantity of interest or an intermediate quantity, whereas according to the prior art it was necessary to carry out a large number of acquisitions in order to obtain, for each pixel, a temporal photon distribution histogram, each histogram then having to undergo digital processing so as to obtain the optical quantity of interest.

It is therefore apparent that the implementation of the method according to the invention makes it possible to substantially reduce the resources or the processing time needed to obtain the optical characteristics of interest.

According to one aspect of the measurement method in accordance with the invention, the illumination comprises the emission of a light pulse of duration p and the acquisition takes place after the emission of the light pulse over a period T=xp and before any new illumination, it being possible for example for x to be chosen so as for example to be greater than 10.

Thus, after a light pulse has been emitted at time $t_0$, the quantity S recorded at each point or pixel of the image will have the value:

$$S = \int_{t_0}^{t_0+T} G(t) H(t) dt$$

in which:
  G(t) is the acquisition modulation function;
  H(t) is the histogram of the photon times of flight on the pixel in question.
  G(t) will hence be a temporal function.

According to the invention, the function G(t) may differ in nature depending on the desired characteristic quantity.

Thus, to obtain the Mellin transform of the H(t) function, a function G(t) of the type $G_k(t)=at^k$ is used, where a is a positive real number and k is an integer. By using such a function it is possible to calculate the $k^{th}$ moment according to the value chosen for k.

To obtain the Laplace transform, the acquisition modulation function is chosen to be of the $G_c(t)=a'e^{-tc}$ type where a' is a positive real number and c is a real number.

By this same method it is also possible to obtain a transform into wavelets such as, for example, spline wavelets, Haar wavelets, Coifmann wavelets and Daubechies wavelets. The acquisition modulation function may also be chosen as a Gaussian wavelet as defined by the formula:

$$G_n(t) = \alpha(-1)^n \frac{d^n e^{\frac{t^2}{2}}}{dt^n}$$

where n is a positive integer or zero.

According to the invention, the modulation function may be a function which is always of the same sign, for example positive, or on the contrary a function having one or more positive parts and one or more negative parts. However, the devices used for modulating the acquisition are not always capable of providing negative modulation values. To solve this problem, according to an implementation variant, the measurement method according to the invention comprises at least:
- a first illumination and acquisition phase during which the acquisition is modulated according to a first acquisition modulation function, and a first image of optical characteristics or quantities of the object is recorded;
- a second illumination and acquisition phase during which the acquisition is modulated according to a second acquisition modulation function, and a second image, of the same size as the first, of optical characteristics or quantities of the object is recorded;
- a step of generating a third image, of the same size as the first, of optical characteristics of the object, said image being obtained by subtracting the second image from the first image.

Thus, if the acquisition modulation function G(t) can be decomposed into a positive part $G_+(t)$ and a negative part $G_-(t)$, the first acquisition may be carried out by implementing the positive part $G_+(t)$ as acquisition modulation function, whereas the second acquisition may be implemented using the absolute value of the function $G_-(t)$ as acquisition modulation function. Thus, the result of the step of generating the third image corresponding to the subtraction of the image of the second acquisition step from the image of the first acquisition step will correspond, for each pixel, to the value that would have been obtained for an acquisition modulated with the function G(t). In this way, it is possible to circumvent the physical impossibilities associated with the acquisition modulation device.

According to one way of implementing the invention, the method comprises:
- several phases illumination and acquisition modulated with recording of an image at each phase; and
- a step of reconstructing the optical characteristics of the object from the recorded images.

Thus, by changing the acquisition modulation function at each illumination/acquisition sequence, it is possible to obtain an optical characteristic of interest which can then be used for reconstructing optical quantities of the object scanned.

According to the invention, the acquisition may be carried out both in transmission and in reflection. When the method is implemented in transmission, the acquisition is then carried out by collecting the photons coming from a face different from that illuminated by the source, for example by the opposite face. In the opposite case, the measurement is said to be in reflection, the illumination and the acquisition both being carried out in such a way that the imager images the face illuminated by the source.

According to one feature of the invention, each recorded image is two-dimensional.

According to the invention, the method may be carried out for conventional optical tomography scanning or else for fluorescence tomography scanning. In the latter case, the object will then comprise at least one fluorescent label.

The invention also relates to a device for measuring optical characteristics of an object located in a measurement area. This measurement device then comprises at least:
- a pulsed light source designed to emit light radiation towards the measurement area;
- means for the acquisition of an image of the measurement area, which comprise a sensor designed to acquire at least one measurement at at least one point or pixel, and acquisition modulation means interposed between the sensor and the measurement area; and
- a control and acquisition unit which is synchronized with the light source and connected to the acquisition sensor and to the acquisition modulation means.

According to the invention, the control and acquisition unit is designed to carry out the acquisition outside the phase of light radiation emission by the light source and to control, at each acquisition, the acquisition modulation means according to a continuous, non-sinusoidal and temporal acquisition modulation function. The temporal modulation function, which is a continuous function, is designed so that each modulated acquisition results directly in an optical characteristic of the object at each point or pixel of the image or an intermediate quantity enabling this characteristic to be calculated more rapidly.

According to the invention, the sensor may be designed to acquire a point or almost point image of the object and will comprise a single pixel or may be likened to a single pixel, i.e. a zero-dimensional sensor. The sensor may also consist of a linear array of point sensors and will then correspond to a row of pixels, i.e. a one-dimensional sensor. The sensor may also comprise a matrix of point sensors and may then correspond to a matrix of pixels, i.e. a two-dimensional sensor. Thus, the term "image" is employed in the context of the description to denote a zero-dimensional, one-dimensional or two-dimensional object, within the context of the acquisition, or even a three-dimensional object after reconstruction.

According to the invention, the acquisition modulation means may be produced in any suitable manner and may for example form an integral part of the sensor, being located upstream of the sensitive surface of the latter or else placed upstream of the sensor in the direction of the photon flux coming from the measurement area.

Thus, according to one embodiment of the measurement device, the acquisition modulation means comprise an image intensifier and means for controlling the gain of the intensifier that are controlled by the control and acquisition unit, which unit is designed to vary the gain of the intensifier in accordance with the acquisition modulation function.

According to another embodiment of the measurement device, the modulation means comprise a variable optical attenuator associated with means for controlling the attenuation coefficient that are controlled by the control and acquisition unit, which unit is then designed to vary the attenuation coefficient in accordance with the acquisition modulation function.

According to one feature of the invention, the control unit, for controlling the measurement device, is designed to implement the measurement method according to the invention.

Of course, the various aspects, variants and embodiments of the measurement device and ways of implementing the measurement method may be combined with one another in various combinations insofar as these aspects, embodiments, ways of implementation and features are not mutually incompatible or exclusive.

Moreover, various other features and advantages of the invention will become apparent from the description above, given with reference to the appended drawings which illustrate various non-limiting embodiments of measurement devices that can be used for implementing the measurement method according to the invention.

The components common to the various figures and embodiments of the invention bear the same numerical references.

DETAILED DESCRIPTION OF THE INVENTION

Figure 1:
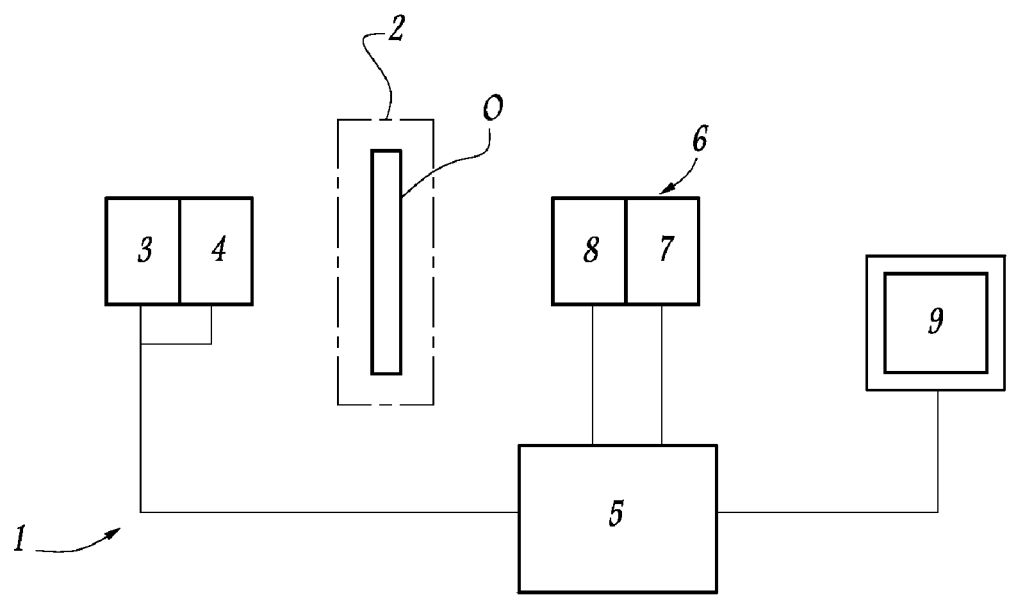
FIG. 1 is a schematic view of a transmission measurement device for measuring the optical characteristics of an object such as, for example, a biological specimen to be scanned or else a test specimen, also called a "phantom" specimen.

A measurement device according to the invention, as illustrated in FIG. 1 and denoted in its entirety by the reference 1, comprises a measurement area 2 depicted schematically by the dot-dash lines, in which an object O is placed, which object may be a specimen of biological or nature or else, optical characteristics of which have to be determined. In the case of in vivo measurement, the object O may also be formed by all or part of a living organism, such as a small animal or part of a human body.

The measurement device 1 comprises a light source 3 designed to emit light radiation toward the measurement area in order to illuminate the object O. The light source 3 is a pulsed source, preferably a subnanosecond pulsed source, and can generate a point of light on at least one face of the object O. It may for example comprise a light source combined with a laser cavity so as to emit pulsed radiation having a wavelength of 635 nm and a pulse repetition frequency of 80 MHz. The light source 3 is associated with synchronization means 4 and is controlled by a control and acquisition unit 5 connected to the synchronization means. One or more optical fibres may guide the light between the light source and at least one part of one face of the object O. In this case, the end of the fibre, or fibres, located close to the object may be likened to a secondary light source.

The measurement device 1 also comprises acquisition means 6 for taking an image of the measurement area 2. According to the example illustrated, the measurement device 1 works in transmission and therefore the light source and the acquisition means are placed on either side of the measurement zone 2 and preferably, but not necessarily, facing one another. The acquisition means 6 then comprise a sensor 7 comprising at least one pixel and preferably, but not exclusively, a two-dimensional matrix of pixels. The term "dimensional matrix" should be understood to mean at least one row of pixels and more particularly preferably an assembly comprising rows of pixels and columns of pixels. The sensor 7 is also controlled by the unit 5, which is designed to control and record the measurements taken by each of the points or pixels of the sensor 7. This sensor 7 produces the image of part of one face of the object O, by means of an optical device, such as one or more lenses or by means of at least one optical fibre. The acquisition means 6 also include acquisition modulation means 8 which are interposed between the sensor 7 and the measurement zone 2. The acquisition modulation means 8 are also controlled by the unit 5, which may furthermore be connected to display means 9, such as a video screen.

The control and acquisition unit 5 may be produced in any suitable manner such as, for example, in the form of a dedicated electronic system or else may be formed by a microcomputer comprising all the acquisition and control cards and calculation, memory and software resources needed to implement the method according to the invention, being in particular designed to control the light source and the excitation modulation means, as well as the acquisition means.

According to the example illustrated, the measurement device 1 works in transmission, and therefore the light source and the acquisition means are placed on either side of the measurement area 2 and preferably, but not necessarily, facing one another.

According to the invention, the acquisition means may be produced in any suitable manner and, within the context of the example illustrated in FIG. 1, the acquisition means 6 comprise a high-speed intensified camera such as, for example, a camera of the "high-rate imager" type sold by Kentech Instrument Limited. Such an intensified camera comprises, as shown schematically in FIG. 2, as acquisition modulation means, a light intensifier tube 8 optically coupled to a sensor, such as a CCD matrix sensor 10. The intensifier tube 8 has, on the face turned towards the incident radiation direction, on the opposite side from the sensor 10, a photocathode 15 intended to emit electrons upon receiving photons. The photocathode 15 is followed by a microchannel plate 16 provided with microchannels 17, the size of which has been intentionally exaggerated in FIG. 2. Downstream of the microchannel plate 16, the tube 8 has a biased fluorescent screen 18 intended to emit photons under the impact of the electrons emanating from the microchannel plate 16. Here, the fluorescent screen 18 is coupled to the sensor 10 via a fibre optic bundle 19, it being understood that the screen 18 could also be in immediate contact with the photosensitive surface of the sensor 9, or coupled with an objective lens. Further to amplify the electrons emitted by the photocathode and to transfer them to the fluorescent screen 18, a constant potential difference is maintained between the photocathode 15 and the front face of the multichannel plate 16 and also between the rear face of the multichannel plate 16 and the fluorescent screen 18. Moreover, a variable potential difference $U_v$ which may be modulated so as to vary the gain G(t) of the intensifier 8, is applied between the front face and the rear face of the multichannel plate 16. The potential difference $U_v$ is controlled by the unit 5.

The measurement device thus constructed is designed to implement the measurement method according to the invention in the following manner.

The laser emits excitation pulses which may have a duration of a few tens of picoseconds, for example between 40 fs and 100 ps, this duration being measured at mid-height of the maximum value of the curve of the instantaneous pulse intensity. Of course, a femtosecond laser may also be used as light source. The laser synchronization provided by the means 4 triggers the acquisition at the sensor 7 for a duration T ranging from about a few nanoseconds to a few tens of nanoseconds, for example a duration of between 5 and 10 ns, which means, for a 50 ps pulse, an acquisition duration of more than 100 times the pulse duration. During this acquisition period elapsing from $t_0$ to $t_0+T$ or, in certain cases, from $t_0+\epsilon$ to $t_0+T$, the unit 5 controls the potential difference $U_v$ between the input and output planes of the microchannel plate 16 so as to vary the gain or the sensitivity of the intensifier 8 according to a continuous temporal modulation law G(t). Thus, the amount of light received on each pixel of the sensor 10 will correspond to:

$$S=\int_{t_0}^{t_0+T}G(t)dt.$$

Depending on the nature of the modulation law G(t), it will then be possible, for example to obtain, directly, without subsequent calculation and for each pixel of the sensor, an optical characteristic of the object O or for example to obtain an intermediate quantity dependent on an optical feature.

Thus, for example, the acquisition modulation function may be chosen as a Mellin transform of the type $G(t)=t^k$.

Figure 3:
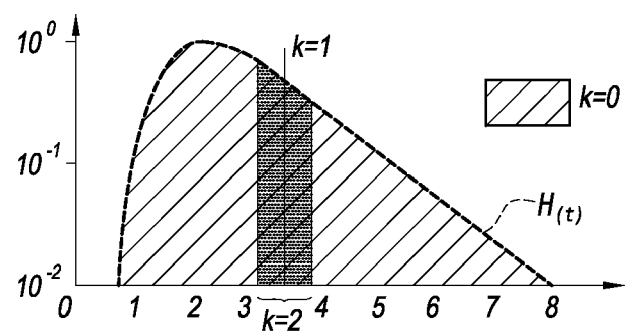
FIG. 3 is a view of a photon time-of-flight histogram H(t) for a point or pixel of the two-dimensional sensor employed by the acquisition means.

During a first acquisition, k may be chosen to have a value of 0 so that the signal S recorded at each pixel of the sensor will be given by:

$$S_0=\int_{t_0}^{t_0+T}H(t)dt$$

which is also called the zero-order moment and corresponds to the integration of the photon times-of-flight, i.e. the hatched area shown in FIG. 3.

During a second acquisition, the value of k may be chosen to be 1 and the measured value S for each pixel will correspond to:

$$S_1=\int_{t_0}^{t_0+T}H(t)dt$$

which is also called the first moment. Thus, by taking the ratio of $S_1$ and $S_0$, the mean photon time-of-flight on the sensor, as shown by the vertical line segment in FIG. 3.

During a third acquisition, k may be chosen equal to 2, and therefore for each pixel of the sensor 9 the measured value will correspond to:

$$S_2=\int_{t_0}^{t_0+T}H(t)dt$$

also called the second moment, which is linked to the variance in arrival of the photons on the sensor 9, as depicted by the dark grey area shown in FIG. 3. The values of the zero-order moment, the first moment and the second moment for each of the pixels may then be used to construct the optical characteristics of the object using mathematical methods called inverse-problem methods, as explained in the publication by F. Lan, S. Lessage and X. Intes "Time domain fluorescent diffuse optical tomography: analytical expressions" published on 4 Apr. 2005 in Volume 13, No. 7, page 2263 of Optics Express, or else given in [3] and the documents of the bibliography of [3].

An acquisition may also be carried out using as acquisition modulation function the function $G(t)=e^{-ts}$ so that the measured value of each pixel will be:

$$S_s=\int_{t_0}^{t_0+T}e^{-ts}H(t)dt$$

which corresponds to a Laplace transform of the histogram H(t) of the photon times-of-flight on each pixel of the sensor.

Figure 4:
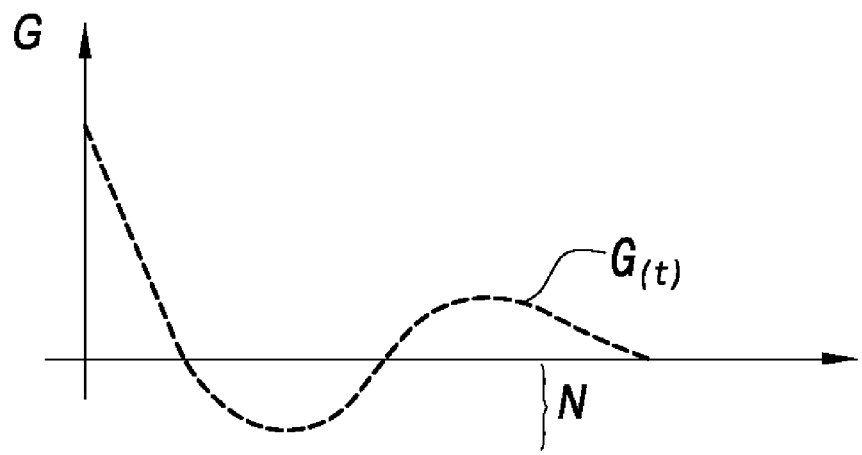
FIG. 4 is a schematic representation of an example of an acquisition modulation law having a positive part and a negative part.
Figure 4:
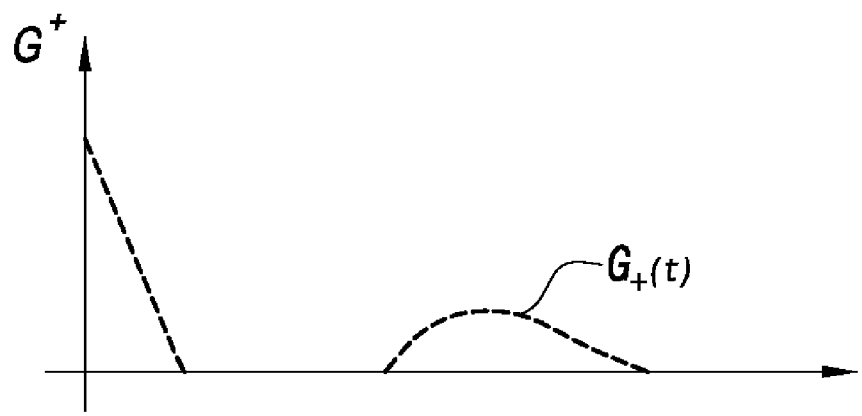
Figure 4:
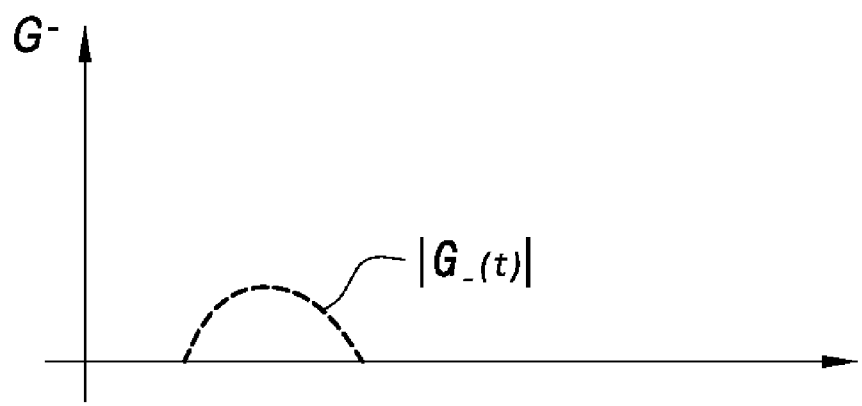

Of course, other types of modulation laws may be carried out, such as for example a modulation law G(t) as illustrated graphically in FIG. 4a. Such a modulation law describes a part $G_+(t)$ of positive gain (FIG. 4b) and a part $G_-(t)$ of negative gain. However, the intensifier tube 16 cannot generate such a negative gain. Therefore, the invention proposes to decompose G(t) in the form $G(t)=G_+(t)+G_-(t)$ where $G_+(t)$ is the positive part of the gain and $G_-(t)$ the negative part of the gain.

An acquisition will therefore be carried out with $G_+(t)$ as modulation function so that, for each pixel of the sensor, the measured quantity will be:

$$S_+=\int_{t_0}^{t_0+T}G_+(t)H(t)dt$$

An acquisition will then be carried out with the absolute value of $G_-(t)$, which is positive, as modulation function so that, for each pixel of the sensor, the measured quantity will be:

$$S_{31}=\int_{t_0}^{t_0+T}|G_-(t)|H(t)dt$$

Finally, by subtracting the two quantities obtained (electronically or numerically in post processing), what is obtained is:

$$S=S_+-S_-=\int_{t_0}^{t_0+T}G_+(t)H(t)dt-\int_{t_0}^{t_0+T}|G_-(t)|H(t)dt=\int_{t_0}^{t_0+T}G(t)H(t)dt$$

which clearly corresponds to a temporal signal weighted by a function that may have negative parts.

In the example described above, according to the invention, the acquisition modulation means are produced in the form of a variable-gain intensifier tube. However, the acquisition modulation means could be produced in another form. Thus, for example, it would be conceivable to place, as acquisition modulation means, an optical attenuator as for example described in the U.S. Pat. No. 7,224,881, controlled by the unit 5. The attenuator may then be placed against the front part of the photocathode of an intensified camera used as sensor.

Figure 6:
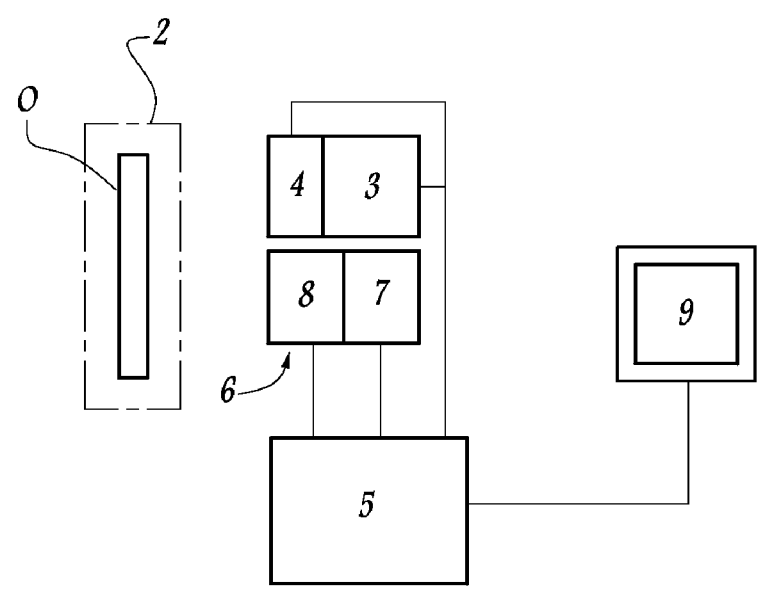
FIG. 6 is a schematic view of a reflection measurement device according to the invention.
Figure 5:
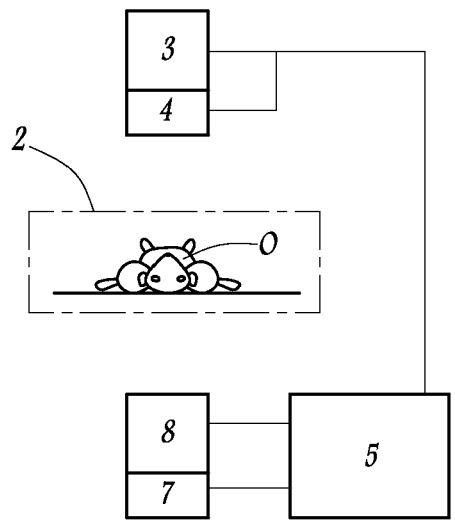
FIG. 5 is a schematic view of an in vivo transmission measurement device.

Moreover, according to the example described in relation to FIG. 1, the measurement device 1 according to the invention is designed to work on specimens. However, the measurement device according to the invention may be used to work on small mammals, as shown in FIG. 5. Likewise, FIG. 6 shows another embodiment of the measurement device according to the invention, designed to work in reflection, the illumination and acquisition means then being located on the same side as the measurement area 2.

The measurement device and the measurement method according to the invention may be used for various applications such as, for example, optical tomography in a scattering medium on humans or animals or in general any other turbid medium. The measurement method and measurement device may also be used in optical fluorescence tomography on humans or animals, or in general any other turbid medium into which fluorophores have been incorporated.

The measurement method and measurement device according to the invention may also be used in optical oxymetry. To do this, a map of the absorption coefficient $\mu_a$ of a medium to be characterized is obtained by using at least two excitation wavelengths and preferably four wavelengths. Such a determination may be carried out by being based for example on determining the absorption coefficient from the moments and the Laplace transform of the function representing the histogram H(t). On this subject, the reader may consult the publication [Schweiger—Applied Optics 97] or Aurélie Laidevant's thesis. The work "Tissue Optics Light Scattering Methods and Instruments for Medical Diagnosis", by Valery Tuchin, Tutorial Texts in Optical Engineering, Volume TT38, published by SPIE Press, may thus be used to solve the linear system of equations which, for each excitation wavelength $\lambda_{ex-n}$, makes, at each point in the medium, the following quantities:

$$\mu_a = c_{H2O}\sigma_{H2O} + c_f\sigma_f + c_{Hb}\sigma_{Hb} + c_{HbO}\sigma_{HbO}$$

$c_{H2O}$=water concentration of the medium;

$c_f$=fat concentration of the medium;

$c_{Hb}$=deoxygenated haemoglobin concentration of the medium;

$c_{HbO}$=oxygenated haemoglobin concentration of the medium;

$\sigma_{H2O}$=water absorption cross section of the medium at the wavelength $\lambda_{ex-n}$;

$\sigma_f$=fat absorption cross section of the medium at the wavelength $\lambda_{ex-n}$;

$\sigma_{Hb}$=deoxygenated haemoglobin absorption cross section of the medium at the wavelength $\pi_{ex-n}$; and $\sigma_{HbO}$=oxygenated haemoglobin absorption cross section of the medium at the wavelength $\lambda_{ex-n}$.

Thus, knowing $\sigma_{H2O}$, $\sigma_f$, $\sigma_{Hb}$, $\sigma_{HbO}$ for each of the four excitation wavelengths and from the evaluation of the absorption coefficient $\mu_a$ of the point in the medium in question, based on four measurements carried out at said four wavelengths, it is possible to obtain the respective water, fat, deoxygenated haemoglobin and oxygenated haemoglobin concentrations and, by so doing, determine for example the haemoglobin saturation $S_{O2}$ according to the expression:

$$S_{O_2}(\%) = \frac{c_{HbO2}}{c_{Hb} + c_{HbO2}} \cdot 100.$$

Thus, a saturation coefficient is obtained at each point in the medium. The expression "point in the medium" is understood to mean an elementary volume of the medium determined by the meshing carried out in order to reconstruct the $\mu_a$ absorption map.

It is also possible to determine an average haemoglobin saturation coefficient of a medium by making four determinations of the average absorption coefficient of the medium at four different wavelengths and then solving the four equations linking respectively, at a given wavelength, the average absorption coefficient $\mu_a$ to the average water, fat, deoxygenated haemoglobin and oxygenated haemoglobin concentrations.

Another possibility of applying the invention is to use only two excitation wavelengths, and thus to neglect $c_{H2O}$, $c_f$, choosing the wavelengths in a region where the absorption due to water and to fat is negligible compared with the absorption due to haemoglobin, whether oxygenated or not. We therefore obtain, at each excitation wavelength $\lambda_{ex-n}$, the equation:

$$\mu_a = c_{Hb}\sigma_{Hb} + c_{HbO}\sigma_{HbO}$$

for each point in the medium, a point in the medium being determined by the meshing carried out in order to reconstruct the $\mu_a$ absorption map.

Next, the following equation is solved so as to obtain the saturation coefficient at each point in the medium:

$$S_{O_2}(\%) = \frac{c_{HbO2}}{c_{Hb} + c_{HbO2}} \cdot 100.$$

It is also possible to determine an average haemoglobin saturation coefficient of a medium, by making two determinations of the average absorption coefficient of the medium at two different wavelengths and then solving the two equations linking respectively, at a given wavelength, the average absorption coefficient $\mu_a$ to the average deoxygenated haemoglobin and oxygenated haemoglobin concentrations.

Figure 2:
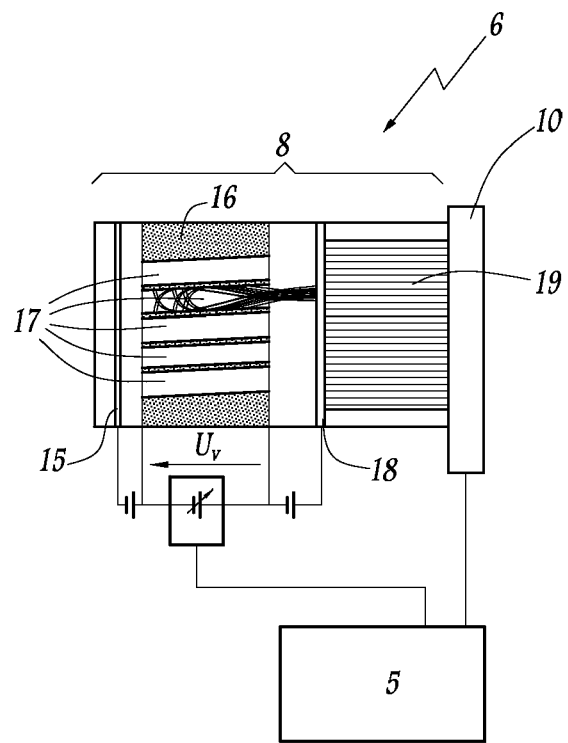
FIG. 2 is a schematic view showing the principle of an intensified camera used as acquisition means of the measurement device illustrated in FIG. 1.

According to the example described in relation of FIG. 2, the integrated modulation and acquisition means 8 comprise an electron-emitting photosensitive surface followed by three electron-accelerating stages, the gain or the sensitivity being modulated by varying the voltage within the microchannel plate. However, the sensitivity may also be modulated by varying the voltage on the photocathode. Likewise, according to the invention, the acquisition modulation means could be produced in another way, for example it may simply comprise a photocathode, a microchannel plate and an anode. The gain or the sensitivity may then be modulated by varying the voltage on the photocathode.

The acquisition modulation means could also comprise several microchannel plates with one or more intermediate electrodes placed between two successive plates. The gain will then be modulated by varying the voltage on each intermediate electrode.

According to the exemplary embodiment described above, the light source is a pulsed source comprising a laser cavity that generates "naturally" pulsed radiation. Such a light pulsed source hence emits successive light pulses. Each pulse will then be preferably a subnanosecond pulse. It should also be pointed out that, according to the invention, the modulated acquisition may start when the light source is turned on, but it will be understood that the most significant part, or even the totality, of the acquisition takes place during the phases when the light source is off, between two successive light pulses of the pulse source. In general, a modulated image acquisition will be taken between each light pulse and the following light pulse. Carrying out the most significant part of the acquisition outside the illumination phase means that at least 80%, preferably at least 90%, of the acquisition duration, is carried out while the light source is off. Preferably, the totality of the acquisition takes place when the light source is turned off.

Of course, it is also conceivable to use a monochromatic or quasi-monochromatic light source having a wavelength other than that mentioned above and a different pulse repetition frequency. It is also conceivable to use a white light source, however, since radiation in the red and in the near infrared is known to penetrate deeply into organic tissue, it will be preferable to use light sources having wavelengths between 620 nm and 2500 nm.

Of course, various other modifications may be made to the measurement method and the measurement device according to the invention within the framework of the appended claims.

The invention may be used in various applications of optical imaging in diffuse media, and especially in tomography applications.

Moreover, the reader may find information regarding diffuse optical imaging in the following publications, the content of which is incorporated by reference into the present application:

Schweiger and Arridge, "Direct calculation with a finite-element method of the Laplace transform of the distribution of photon time-of-flight in tissue", Applied Optics 97, Vol. 36, No. 34, 1 Dec. 1997;

Gributs and Burns, "Haar transform analysis of photon time-of-flight measurements for quantification of optical properties in scattering media", Applied Optics 03, Vol. 42, No. 16, 1 Jun. 2003.

The invention claimed is:

1. A method of measuring optical characteristics of an object, comprising the following operations:
   illumination of the object by means of a pulsed light source; and
   acquisition of an image by modulated detection of light rays coming from the object consecutively to the illumination, the detection being modulated according to an acquisition modulation function G(t) which is continuous, non-sinusoidal and temporal, the acquisition taking place outside the phase of illumination by the light source.

2. The method according to claim 1, wherein the light source is a subnanosecond pulsed source and in that the acquisition is carried out between two successive light pulses of the light source.

3. The method according to claim 1, wherein the acquisition modulation function G(t) is chosen from the following functions:
   $G_k(t) = at^k$ in which a is a positive real number and k is an integer;
   $G_c(t) = a'e^{-tc}$ where a' is a positive real number and c is a real number; and
   G(t) is a wavelet.

4. The method according to claim 1, wherein it comprises:
   a first illumination and acquisition phase during which the acquisition is modulated according to a first acquisition modulation function, and a first image of optical characteristics of the object is recorded;
   a second illumination and acquisition phase during which the acquisition is modulated according to a second acquisition modulation function, and a second image, of the same size as the first, of optical characteristics of the object is recorded;
   a step of generating a third image, of the same size as the first, of optical characteristics of the object, said image being obtained by subtracting the second image from the first image.

5. The method according to claim 1, wherein it comprises:
   several phases of illumination and acquisition modulated with recording of an image at each phase;
   a step of reconstructing the optical characteristics of the object from the recorded images.

6. The method according to claim 1, wherein each recorded image is two-dimensional.

7. The method according to claim 1, wherein the object includes at least one fluorescent label.

8. The method according to claim 1, wherein the acquisition takes place on the opposite side of the illumination with respect to the object.

9. The method according to claim 1, wherein the acquisition and the illumination take place on the same side of the object.

10. A device for measuring optical characteristics of an object located in a measurement area, comprising:
    a pulsed light source designed to emit light radiation towards the measurement area;
    means for the acquisition of an image of the measurement area, which comprise a sensor designed to acquire at least one measurement at least one point or pixel, and acquisition modulation means interposed between the sensor and the measurement area; and
    a control and acquisition unit which is synchronized with the light source and connected to the acquisition sensor and to the acquisition modulation means and which is designed to carry out the acquisition outside the phase of light radiation emission by the light source and to control, at each acquisition, the acquisition modulation means according to an acquisition modulation function G(t) which is continuous, non-sinusoidal and temporal.

11. The device according to claim 10, wherein the light source is a subnanosecond pulsed source and the control unit is designed to carry out the acquisition between two successive light pulses of the light source.

12. The device according to claim 10, wherein the sensor is designed to acquire several measurements at several points or pixels.

13. The device according to claim 10, wherein the acquisition modulation means comprise an image intensifier and means for controlling the gain of the intensifier that are controlled by the control and acquisition unit, which unit is designed to vary the gain of the intensifier in accordance with the acquisition modulation function G(t).

14. The device according to claim 10, wherein the acquisition modulation means comprise a variable optical attenuator associated with means for controlling the attenuation coefficient that are controlled by the control and acquisition unit, which unit is designed to vary the attenuation coefficient in accordance with the acquisition modulation function.

15. The device according to claim 10, wherein the control unit is designed to implement the method according to claim 1.

16. The device according to claim 10, wherein the light source and the acquisition means are placed on either side of the measurement area.

17. The device according to claim 10, wherein the light source and the acquisition means are placed on the same side of the measurement area.

* * * * *